US00PP25151P3

(12) United States Plant Patent
Grosser

(10) Patent No.: US PP25,151 P3
(45) Date of Patent: Dec. 9, 2014

(54) PUMMELO TREE NAMED '5-1-99-5'

(50) Latin Name: ***Citrus grandis* (L.) Osbeck**
Varietal Denomination: 5-1-99-5

(75) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 299 days.

(21) Appl. No.: 13/506,364

(22) Filed: Apr. 13, 2012

(65) Prior Publication Data

US 2013/0276180 P1 Oct. 17, 2013

(51) Int. Cl.
*A01H 5/00* (2006.01)

(52) U.S. Cl.
USPC ..... Plt./201

(58) Field of Classification Search
USPC ..... Plt./201
See application file for complete search history.

(56) References Cited

PUBLICATIONS

Zheng et al., "Comparative transcript profiling of a male sterile cybrid pummelo and its fertile type revealed altered gene expression related to flower development," *PLOS One,* 7(8):1-13, 2012.
Grosser et al., "Highlights from the UF/IFAS/CREC Citrus Improvement Program," presentation at the Florida Citrus Show, Ft. Pierce, Florida, Jan. 19-20, 2011.

*Primary Examiner* — Kent L Bell
(74) *Attorney, Agent, or Firm* — Dentons US LLP

(57) ABSTRACT

A new red pummelo tree particularly distinguished by producing delicious and juicy red-fleshed fruit in central Florida, is disclosed.

5 Drawing Sheets

Latin name of the genus and species of the plant claimed: *Citrus grandis* (L.) Osbeck.

Variety denomination: '5-1-99-5'.

BACKGROUND OF THE INVENTION

The present invention relates to a new and distinct cultivar of pummelo tree, botanically known as *Citrus grandis*, and hereinafter referred to by the name '5-1-99-5'. Cultivar '5-1-99-5' is a red pummelo selected from a group of open-pollinated seedlings obtained from the 'Hirado Buntan Pink' pummelo (female parent), currently the most popular variety and the only commercially significant pummelo in Florida. Fruit of '5-1-99-5' is quite different from that of 'Hirado Buntan'. The fruit flesh is light pink for 'Hirado Buntan', and an attractive dark red for '5-1-99-5'. Fruit rind of relatively thin for both of these pummelos as compared to pummelos in general, but '5-1-99-5' generally has a thinner rind than 'Hirado Buntan'. Fruit shape is also different, as 'Hirado Buntan' generally has a flatter fruit than '5-1-99-5', which is a bit more oblong. Fruit size is quite uniform for '5-1-99-5' and quite variable for 'Hirado Buntan'. Average fruit size is larger for '5-1-99-5'. Flavor also differs, with '5-1-99-5' having more of a hint of 'grapefruit' flavor. '5-1-99-5' was asexually propagated by standard inverted-T grafting to sour orange+Carrizo somatic hybrid rootstock and planted in Lake Alfred, Fla., where trees demonstrated all the characteristics of the original plant.

SUMMARY OF THE INVENTION

The following are the most outstanding and distinguishing characteristics of this new cultivar when grown under normal horticultural practices in Florida. '5-1-99-5' is a medium-large sized pummelo with thinner rind than most favored pummelo selections known to the Inventor. '5-1-99-5' features attractive dark red-fleshed segments that are more uniform in size and shape than other pummelos known to the Inventor. '5-1-99-5' has a delicious flavor with just a hint of grapefruit bitterness. '5-1-99-5' fruit is quite juicy and fruit size is very uniform. Fruit on the tree sometimes exist in clusters, and the rind can exhibit pink blushes where fruit are touching.

BRIEF DESCRIPTION OF THE DRAWINGS

This new red pummelo plant is illustrated by the accompanying photographs which show the plant's form, foliage, and fruit. The colors shown are as true as can be reasonably obtained by conventional photographic procedures. All photographs were taken in November of 2010.

DETAILED BOTANICAL DESCRIPTION

Figure 1:
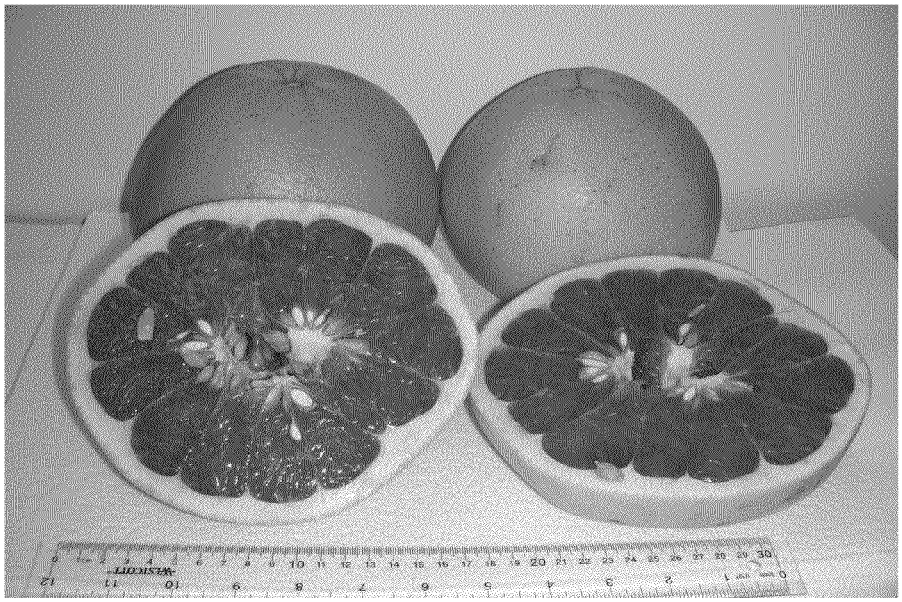
FIG. 1. Shows whole and cut fruit of '5-1-99-5'.
Figure 2:
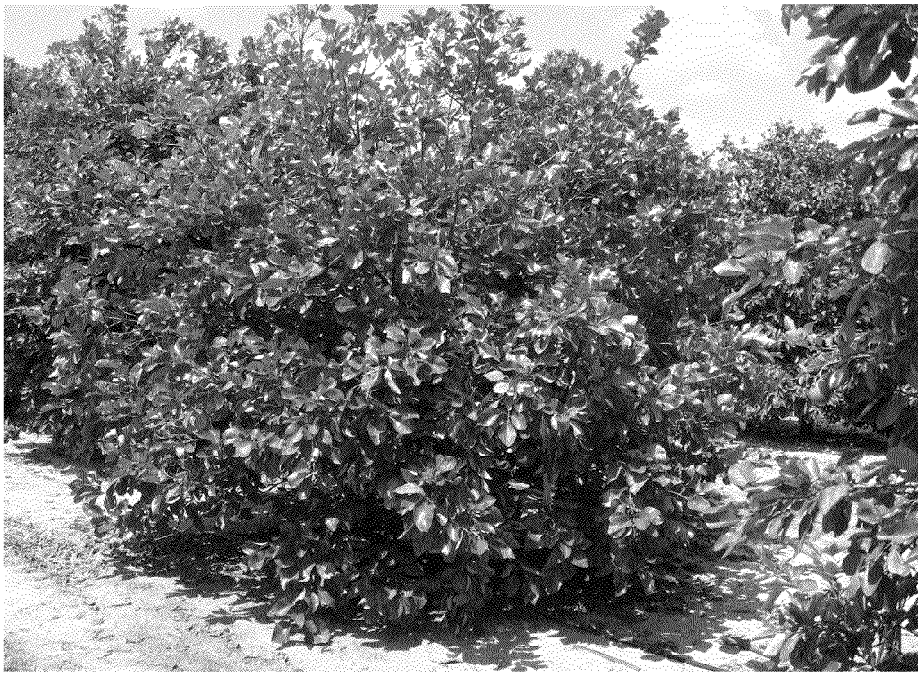
FIG. 2. Shows a tree showing overall plant habit, including foliage and fruit.
Figure 3:
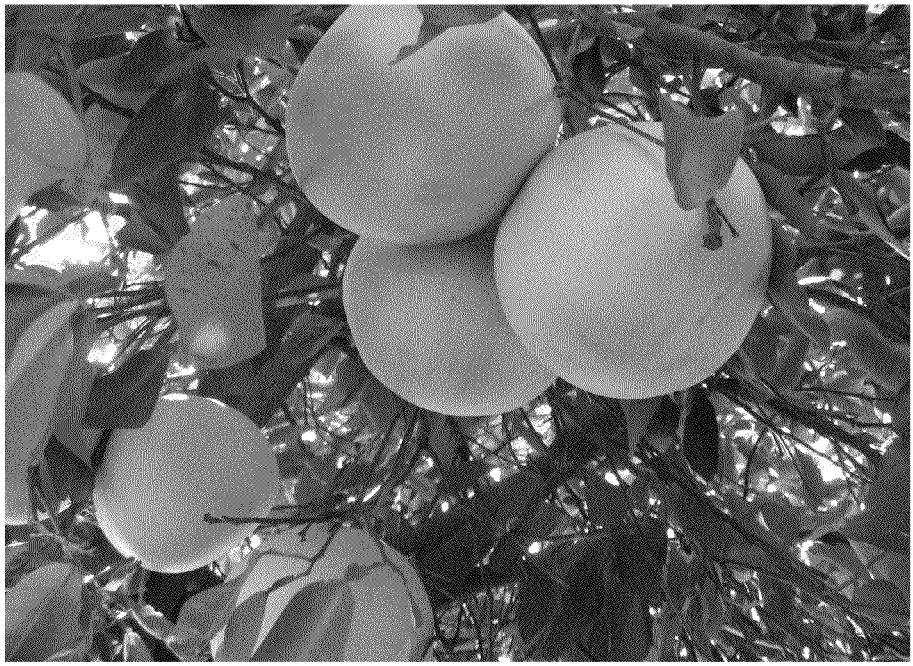
FIG. 3. Shows a cluster of fruit on a '5-1-99-5' tree.
Figure 4:
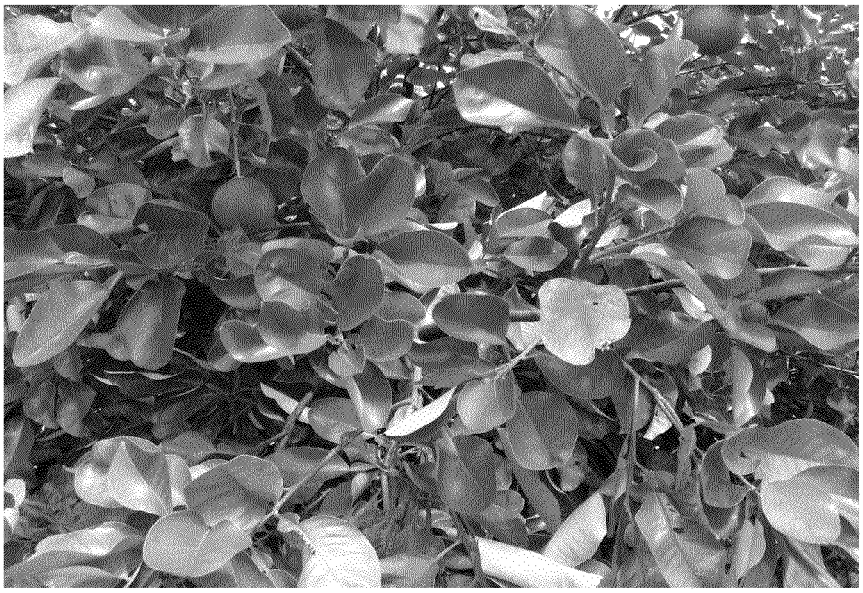
FIG. 4. Shows mature leaves and immature fruit.
Figure 5:
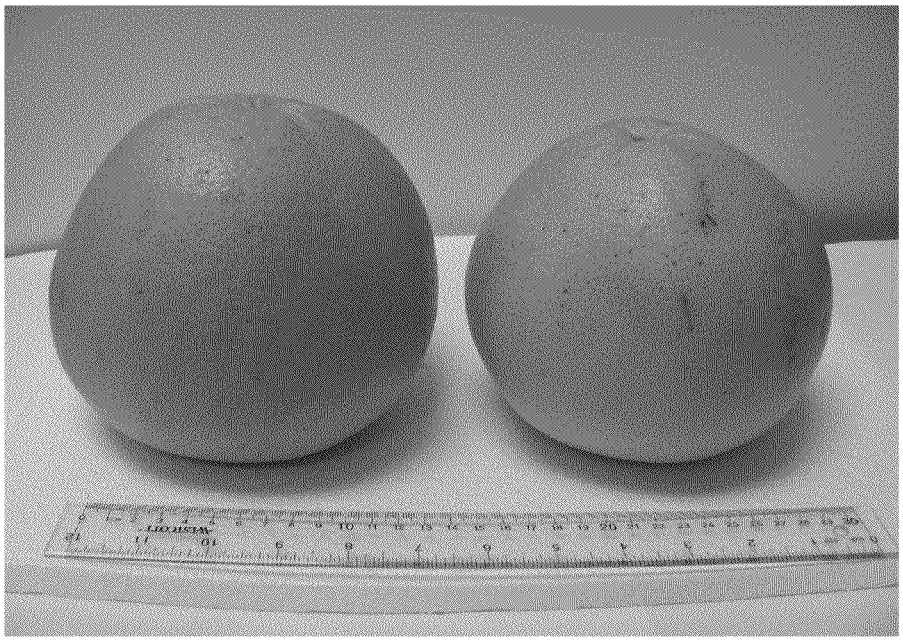
FIG. 5. Shows a fruit of '5-1-99-5'.

The following detailed description sets forth the distinctive characteristics of '5-1-99-5'. The present botanical description is that of the variety grown on an 8-year-old tree on 'Swingle' citrumelo rootstock (*C. paradisi*×*Poncirus trifoliata*) in Lake Alfred, Fla. The colors (except those in common terms) are described from R.H.S. Colour Chart published by The Royal Horticultural Society in London (second edition), in association with the Flower Council of Holland. Phenotypic Description of *Citrus grandis* (L.) Osbeck ('5-1-99-5').

Classification:

*Botanical.*—*Citrus grandis* (L.) Osbeck.

*Common name.*—Pummelo.

Parentage:

*Female parent.*—'Hirado Buntan Pink' pummelo.

*Male parent.*—Unknown.

Tree:

*Ploidy.*—Diploid.

*Size.*—Large, with heights of 3.35 meters currently unpruned.

*Tree spread.*—Tree spread reaches 3.4 meters.

*Vigor.*—Vigorous, growing shoots of 0.6 meters or more in typical new leaf flush from the current tree.

*Density.*—Canopies are quite dense with open canopy.

*Form.*—The shape of the tree is obloid with upright branches grown, branch growth toward medium angles. Branches exhibit drooping after fruit has commenced.

*Growth habit* (*current season*).—Branches grow laterally, and more branches droop as fruits grow bigger.

Trunk and branches:

*Trunk diameter.*—Trunk diameter reaches 13 cm at 30 cm above the ground.

*Trunk texture.*—Smooth.

*Trunk bark color.*—RHS 197A (greyed-green); irregularly striated with N189A (greyed-green) and RHS N189C (greyed-green).

*Branch length.*—Branch length reach 3.5 meters from the first crotch point to the tip of the branch.

*Branch texture.*—Relatively smooth with small thorns or spines at each leaf knot.

*Branch color* (*shoots from previous flush, hardened and 4 mm to 5 mm in Diameter*).—RHS 138S (green).

*Crotch angle.*—Tree crotch forms 30 degree angle from the main trunk.

*Branch diameter.*—5.8 mm to 6.6 mm.

*Internode length.*—25 mm to 36 mm.

Leaves:

*Size* (*lamina average*).—Length: 120 mm. Width: 76 mm. L/W ratio: 1.5 to 1.6.

*Thickness.*—Regular and average for commercial pummelo.

*Type.*—Simple.

*Shape.*—Elliptical.

*Apex.*—Retuse.

*Base.*—Acute to sub-obtuse.

*Margin.*—Entire, smooth and very slightly undulated.

*Surface.*—Upper surface: Glabrous. Lower surface: Large veins that are pinnately netted.

*Color.*—Upper surface (adaxial): RHS 138A (green). Lower surface (abaxial): RHS 144b (yellow-green).

*Petiole.*—Shape: Brevipetiolate (shorter than leaf lamina); junction between petiole and lamina is articulate. Width (petiole wing): Wide, compared to sweet oranges and mandarins. Shape (petiole wing): Obovate. Length: 40 mm to 45 mm. Width: 20 mm to 28 mm. Color: RHS 138A (green).

Flowers:

*Type.*—Hermaphrodite.

*Bearing.*—Flower clusters grow from leaf axillaries and branch terminals, each flower branch consisting of 2-5 flower clusters, one cluster normally consisting of 7-10 flowers.

*Flower born.*—Flower branch derived from the stems of flush of previous year.

*Diameter.*—Fully opened flowers average 43 mm to 52 mm.

*Depth.*—Typical flower depth averages between 22 mm to 26 mm.

*Flower bud.*—Initial visible flower bud shape: Round dome shaped. Initial visible flower bud length: 3-4 mm. Initial visible flower bud diameter: 3 mm. Mature flower bud shape (before opening): enlongated olive shape. Mature flower bud length (before opening): 18 mm to 19 mm. Mature flower bud diameter (before opening): 12.5 mm-13 mm.

*Color.*—RHSNN145A (yellow-green) for initial visible flower bud.

*Petals.*—Number: 5. Shape: Flat spatula shaped. Apex shape: Smooth acute shaped. Base shape: Even Obtuse. Color: Upper surface: RHS 155B (white). Lower surface: RHSNN155C (white) with yellow-green (RHS 150A) spots distributed in the middle section of the petal toward to the petal apex. Margin: Smooth. Length: 22 mm. Width: 8 mm.

*Calyx.*—Size: Large. Length: 13.6 mm. Diameter: 7.8 mm to 8.2 mm.

*Sepal.*—Number: 4 per flower. Shape: Short flat delta shaped with short acute angle at the apex. Length: 4.9 mm. Width: 7.6 mm. Apex shape: Acute triangle shape. Margin: Smooth. Color: RHS 145C (yellow-green). Upper surface (portion near the tip of the flower sepal): RHS 149C (yellow-green). Lower surface (portion near to the bottom of the flower sepal): RHS 145D (yellow-green).

*Pedicel.*—Length: 13.7 mm to 15.4 mm. Diameter: 1.9 mm to 2.5 mm. Color: RHS 142C (green).

*Flower blooming period.*—First bloom: around late March to early April in central Florida. Full bloom: In 2010, observed full bloom in mid-April.

*Fragrance.*—Very fragrant compared to other citrus blossoms.

Reproductive organs:

*Fertility.*—Self-fertile.

*Stamen.*—Number: 25-27. Length: 12.8 mm to 14.2 mm.

*Pistil.*—Number: 1. Color: RHS 142D (green). Length: 12 mm. Diameter: 2.0 mm to 2.7 mm.

*Stigma color.*—RHS 154C (yellow-green).

*Style.*—Length: 8.5 mm. Diameter: 2.0 mm to 2.4 mm. Color: RHS 142D (green).

*Ovary.*—Shape: Oval shaped. Diameter: 3.8 mm to 5 mm. Color: RHS 144D (yellow-green).

*Anther.*—Length: 1.6 mm. Width: 0.65 mm. Color: RHS 13C (yellow).

*Anther filament length.*—8.3 mm to 10.3 mm.

*Pollen amount.*—Abundant.

*Pollen color* (*general*).—RHS 12A (bright-yellow).

Fruit:

*Size.*—Uniform (more so than most other pummelo cultivars), 160 mm to 180 mm in diameter, 140 mm to 160 mm in tall.

*Fruit weight.*—Averages 1,700 grams.

*Shape.*—Round and slightly bell shaped.

*Shape* (*cross-section*).—Nearly round.

*Apex.*—Truncated with shallow dent mark.

*Apex cavity diameter.*—None.

*Base.*—No neck, with slightly rough peel surface.

*Base cavity diameter.*—9.7 mm.

Harvest: Mid-October through January (affected by rootstock).

Fruit stem (short stem connecting fruit to the branch):

*Length.*—24 mm.

*Diameter.*—7.5 mm.

*Color.*—RHS 188A (grey-green) with RHS 199D (grey-brown) strip.

Rind:

*Adherence.*—Albedo (mesocarp) to fresh (endocarp) is strong compared to mandarins, but similar to grapefruit.

*Thickness.*—8 mm to 10 mm, thinner than most other common pummelo varieties known to the Inventor.

*Texture.*—Medium firm, softer when fully ripe.

*Color.*—Flavedo (epicarp): Range from between RHS 1C (green-yellow) to RHS 2B (yellow). Albedo (mesocarp): RHS 36D (red) to RHS 36A (red). Stylar end: Closed.

Rind oil cell density: 70 to 84 oil cells per square centimeter.

Flesh:

*Number of segments.*—Average between 12 and 13 segments per fruit.

*Typical shape of flesh segments.*—Wedge-shaped.

*Segment length.*—120 mm to 150 mm.

*Segment width.*—35 mm to 60 mm on average.

*Segment walls.*—Strong compare to grapefruit varieties with sufficient strength to maintain integrity as separated.

*Juice.*—Abundant.

*Color.*—Uniformly RHS 39A (red).

*Texture.*—Medium-soft and able to maintain flesh integrity as separated from segment wall.

*Vesicles.*—Medium-thick. Length: averages 18 mm to 26 mm. Diameter: averages 3.8 mm to 7 mm.

Flavor and quality: Excellent flavor from mid-October through January (data from Jan. 4, 2010).

*Brix/acid ratio.*—10.

*Acidity (average).*—1.1. The citric acid content of a juice sample can be determined through a titration of the juice, which involves a certain volume of juice having a base of a known concentration added to it until such point is reached in which all of the acid in the juice is neutralized, known as the endpoint corresponding to the range of phenolphthalein indicator.

*Sucrose content.*—11.0. Refers to a measurement of sucrose content. The pure sucrose or soluble solids value of a juice or citrus product can be determined using a refractometer along with the International Scale of Refractive Indices of Sucrose Solutions, and to which the applicable correction for acidity is added. The Brix value is determined in accordance with the refractometer method outlined in the Official Methods of Analysis of AOAC INTERNATIONAL, Volumes I & II.

*Color score.*—43.2-45.0 (slightly variable per fruit). Refers to a measurement of color for citrus juices, which was obtained using a HunterLab Model D45 Citrus Colorimeter to determine the color score of juice of '5-1-99-5', standardized using Citrus Red (CR) and Citrus Yellow (CY) with an OJ4 color tube indexed for the instrument. For the HunterLab Model D45 Citrus Colorimeter, the color number is equal to 22.510 plus 0.165CR plus 0.111CY.

Seeds:

*Type.*—Monoembryonic.

*Number.*—Ranges from 120 to 130.

*Shape.*—Various in Clavate/club shaped to deltoid-shaped.

*Size.*—Length: 15 mm to 18 mm. Width: 7 mm to 9 mm.

*Seed coat color.*—Outer Surface: RHS 158A (yellow-white) and slightly wrinkled. Inner surface: RHS 164B (greyed-orange).

*Cotyledon color.*—RHS NN155A (white).

Disease/pest resistance: '5-1-99-5' has shown good canker tolerance, much better than that of grapefruit. The female parent of '5-1-99-5', 'Hirado Buntan', is quite susceptible to Huanglongbing (HLB) or citrus greening disease. Red pummelo '5-1-99-5' appears to be slightly more tolerant of HLB, although not as tolerant as other red pummelos.

Hardiness zone: Trees of '5-1-99-5' have shown no signs of cold-susceptibility in the Lake Alfred area of central Florida. The hardiness zone should include all of south and central Florida. '5-1-99-5' has not been tested in north Florida.

Fruit keeping quality: Fruit of '5-1-99-5' retain good quality hanging on the tree for several months after reaching maturity, and also perform very well in cold storage under routinely used storage procedures.

What is claimed is:

1. A new and distinct red pummelo tree as shown and described herein.

* * * * *